(12) United States Patent
Verhulst et al.

(10) Patent No.: US 6,170,536 B1
(45) Date of Patent: Jan. 9, 2001

(54) METHOD AND APPARATUS FOR OPTICALLY MONITORING FILING YARNS (75) Inventors: Joseph Verhulst, Zillebeke; Jozef Peeters, Ypres; Frans Vandenabeele, Zonnebeke-Beselare, all of (BE)

(73) Assignee: Picanol N.V., Ypres (BE)

( * ) Notice: Under 35 U.S.C. 154(b), the term of this patent shall be extended for 0 days.

(21) Appl. No.: 09/308,638

(22) PCT Filed: Nov. 27, 1997

(86) PCT No.: PCT/EP97/06627
§ 371 Date: May 28, 1999
§ 102(e) Date: May 28, 1999

(87) PCT Pub. No.: WO98/24957
PCT Pub. Date: Jun. 11, 1998

(30) Foreign Application Priority Data

Dec. 2, 1996 (BE) .................................. 9601003

(51) Int. Cl.[7] .................................. D03D 51/34
(52) U.S. Cl. .................. 139/370.2; 250/559.15; 250/559.4
(58) Field of Search ............... 139/370.2; 250/559.15, 250/559.4

(56) References Cited

U.S. PATENT DOCUMENTS

| | | | |
|---|---|---|---|
| 3,853,408 | * 12/1974 | Kaalverink | 356/199 |
| 4,716,942 | * 1/1988 | Jensen et al. | 139/370.2 |
| 5,063,973 | * 11/1991 | Kitamura et al. | 139/370.2 |
| 5,136,499 | * 8/1992 | Rydborn | 364/185 |
| 5,251,673 | * 10/1993 | Adachi et al. | 139/370.1 |
| 5,329,961 | * 7/1994 | Bouvyn et al. | 139/370.2 |

* cited by examiner

Primary Examiner—Andy Falik
(74) Attorney, Agent, or Firm—Bacon & Thomas, PLLC (57) ABSTRACT

Method and apparatus for optically monitoring filling yarns inserted into a guide duct (10). Substantially collimated light rays are generated and directed transversely to the guide duct (10) onto photo-detectors (23), with the detection of interruption of the light rays by the fillings determining those positions which are assumed by the fillings when being inserted into the guide duct (10).

11 Claims, 7 Drawing Sheets

METHOD AND APPARATUS FOR OPTICALLY MONITORING FILING YARNS

BACKGROUND OF THE INVENTION

1. Field of the Invention

The invention relates to a method and apparatus for optically monitoring filling yarns, hereafter "fillings", being inserted into a shed using essentially collimated light rays directed transversely to a guide duct onto photo-sensitive detectors, with detection of the interruption of the light-beams by fillings, and to a detector with which to implement the method.

2. Description of the Related Art

It is known form U.S. Pat. No. 3,853,408 to direct a bundle of collimated light rays transversely to a filling guide-duct onto a plurality of photo-detectors mounted in a row transversely to the guide duct. Interruption by a filling of the light beams to the photo-detectors is detected and so processed by an analyzer that the presence of a filling is recognized.

SUMMARY OF THE INVENTION

The objective of the invention is to improve the method of the initially cited kind.

This problem is solved in that the particular filling positions shall be detected which these fillings assume when being inserted into the guide duct.

The method of the invention not only allows detecting the presence of a filling, but also and foremost its position in the guide duct.

In an implementation of the invention, when two or more fillings are inserted simultaneously, the positions of all fillings and hence the presence of all fillings shall be detected.

In another implementation of the invention, the filling positions shall be detected twice or more in sequence during insertion. As a result, not only is it possible to distinguish whether a filling was in fact inserted, or for instance if only a filling fluff or a filling segment moved through the guide duct, but also changes in the filling positions in this guide duct. Moreover advantageously, filling insertion shall be monitored when two or more fillings are inserted simultaneously. Because the fillings move relative to one another when being inserted into the yarn guide duct, it is possible therefore to ascertain during one of the detection procedures whether two or more fillings lie adjacent to each other, that is, whether two or more fillings are present.

To facilitate adjusting the device inserting the fillings, another implementation of the invention provides that the filling positions during one insertion and/or changes in the filling positions shall be displayed. As a result and for instance in the case of an airjet weaving machine, herein loom, an operator is able to so set the functions of the main and auxiliary airjet nozzles that the fillings shall be inserted into a specified zone of the guide duct.

The problem is solved by a filling detector in which an analyzer is fitted including a device for determining the filling's positions when they enter the guide duct.

BRIEF DESCRIPTION OF THE DRAWINGS

Further features and advantages of the invention are shown in the following description of the illustrative embodiments shown in the drawings.

DETAILED DESCRIPTION OF THE PREFERRED EMBODIMENTS

Figure 1:
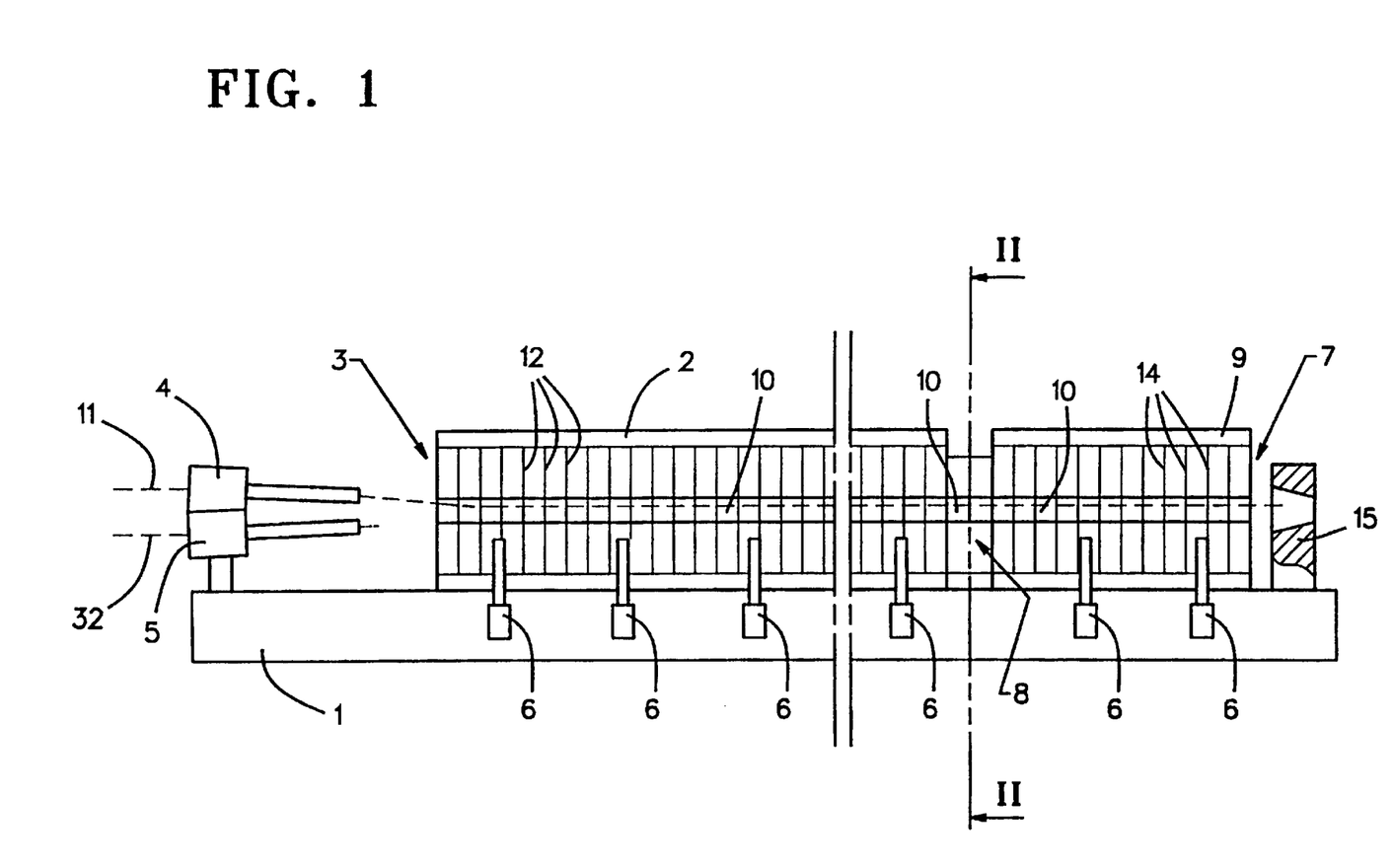
FIG. 1 schematically shows part of a loom fitted with a filling detector of the invention.

FIG. 1 shows a loom's batten 1 to which is mounted a reed 2. Two main jet nozzles 4, 5 are mounted at the insertion side 3. Several auxiliary jet nozzles 6 are mounted along the reed 2 on the batten 1. A filling detector 8 is mounted on the side 7 opposite the insertion side longitudinally after the reed. The filling detector 8 is followed after the length of the reed 2 by a so-called auxiliary reed 9 along which auxiliary jet nozzles 6 also are mounted.

Figure 2:
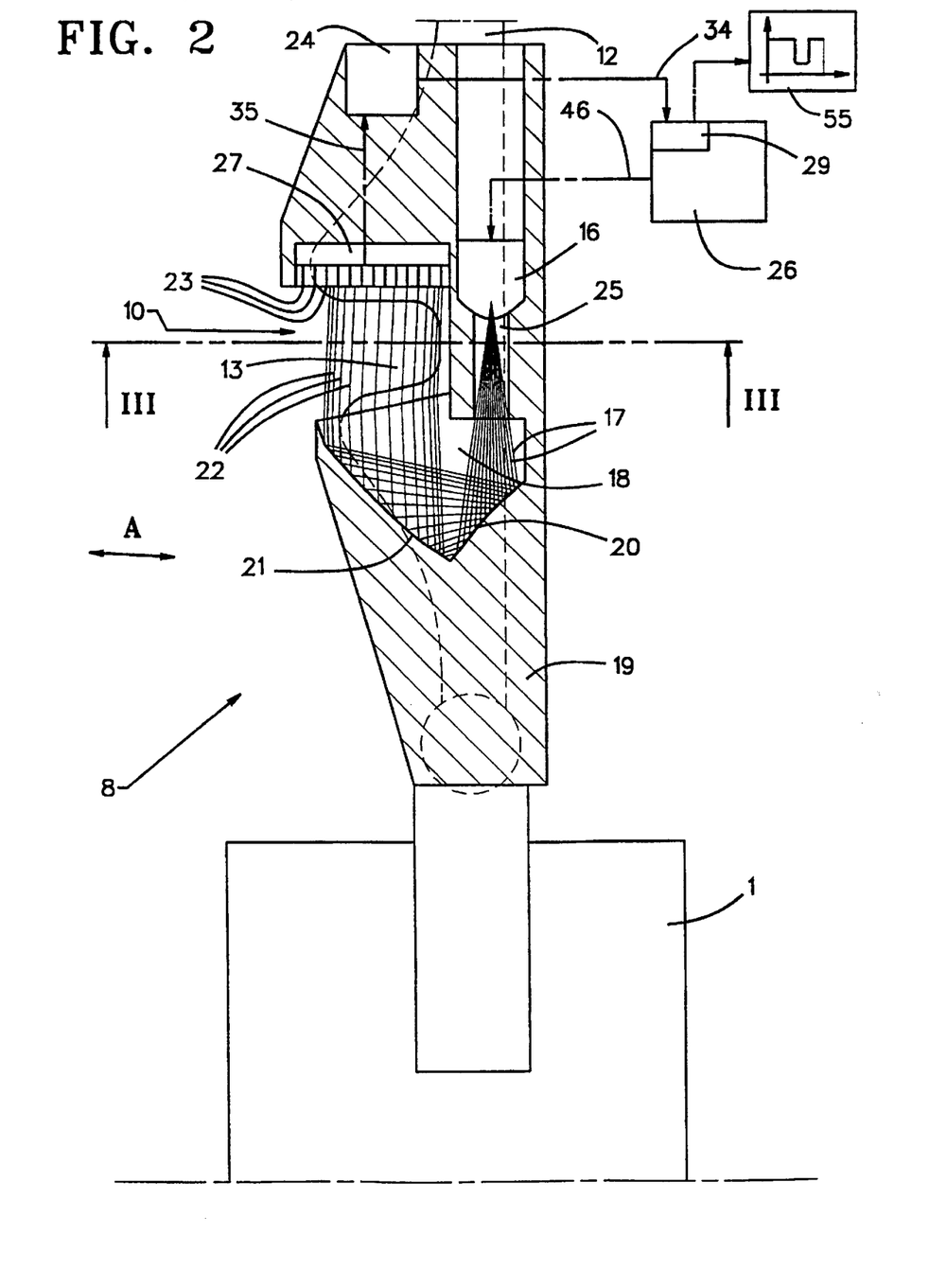
FIG. 2 is a section along line II—II of FIG. 1 on a larger scale.

The fillings 11, 32 blown-in by the main jet nozzles 4, 5 are guided inside a guide duct 10 from the insertion side 3 to the opposite side 7. The guide duct 10 is also shown in FIG. 2 and is constituted of U-shaped cutouts in the dents 12 of the reed 2, of a clearance 13 in the filling detector 8 and of U-shaped cutouts in the dents 14 of the auxiliary reed 9 corresponding to the dents 12 of the reed 2. The U-shaped cutouts of the dents 12 of the reed 2 and of the dents 14 of the auxiliary reed 9 and the clearance 13 of the filling detector 8 are configured consecutively in a row. A filling 11, 32 is blown-in in a known manner by the main jet nozzle 4 or 5 and the auxiliary jet nozzles 6 through the guide duct 10 from the insertion side 3 to the opposite side 7. In general a so-called stretching nozzle 15 is mounted longitudinally after the auxiliary reed 9 on the batten 1 to keep the inserted filling 11, 32 taut after its insertion.

Figure 3:
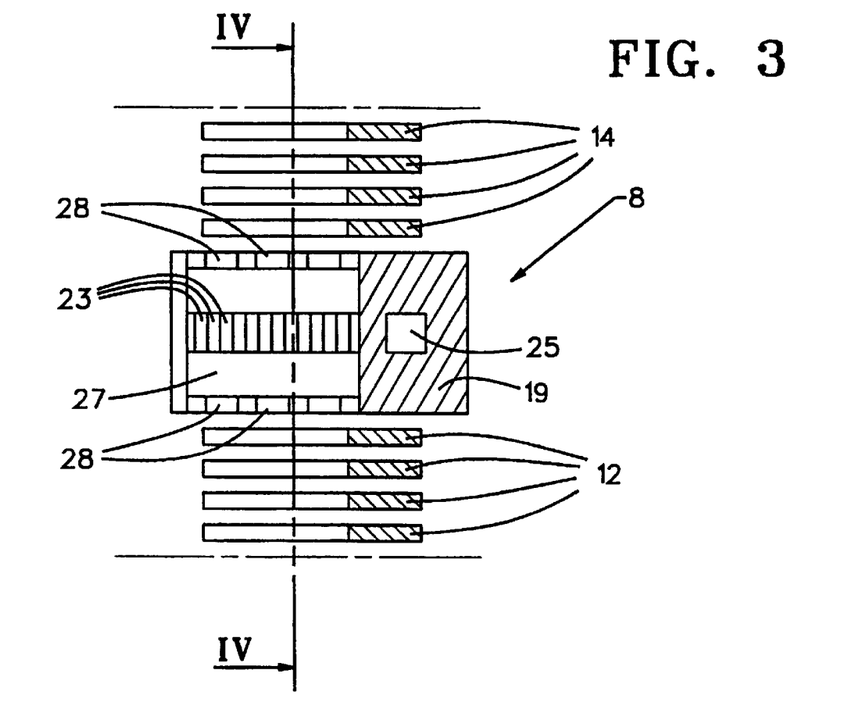
FIG. 3 is a section along line III—III of FIG. 2.
Figure 4:
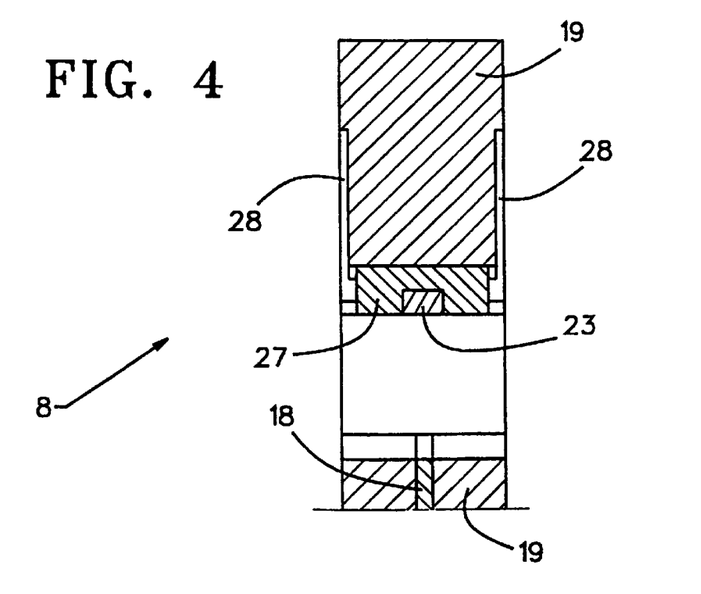
FIG. 4 is a section along line IV—IV of FIG. 3.

The filling detector 8 of FIGS. 2 through 4 contains a light source 16 generating a bundle of light rays 17 directed onto a prism 18 mounted in the housing 19 of the filling detector 8. The light rays are deflected by curved mirrors 20, 21 from below to above to the clearance 13 of the filling detector 8 and as a result they pass inside the portion of the guide duct 10 formed by the clearance 13 substantially from below to above and run substantially parallel to one another. The mirrors 20, 21 may consist of curved facets of the prism 18 coated with a specular material. Preferably the housing 19 is made of plastic to allow casting the prism 18. The refraction of the prism 18 and the curvature of the mirrors 20, 21 are selected in such manner that the light rays 22 shall be substantially collimated and form a beam across the depth (direction of arrow A in FIG. 2) of the guide duct 10.

The filling detector 8 contains a plurality of photo-detectors 23 to detect the substantially collimated light rays 22. The photo-detectors 23 are mounted in the vicinity of the upper boundary of the guide duct 10 and are substantially configured in a row running transversely to the guide duct 10 in the direction of its depth (direction A), and as a result the light rays 22 impinge on the photo-detectors 23. The photo-detectors 23 are connected to an amplifier 24 housed in the housing 19. Illustratively the photo-detectors 23 are photo-electirc sensors emitting a voltage proportional to the light intensity of the light rays 22 incident on them.

The light source 16 consists of a bulb or a light-emitting diode (LED) mounted in the housing 19. The housing 19 is fitted with an aperture 25 to allow the light rays 17 from the light source 16 to reach the prism 18. The light source 16 is connected by electrical leads 46 to a loom control unit 26 also receiving and processing signals from the amplifier 24.

By selecting an appropriate curvature for the mirrors 20, 21, light rays 22 may be generated which not only are substantially collimated but also fill the guide duct across its width at essentially constant light intensity. For that purpose the mirrors 20, 21 may be designed in such manner that they concentrate the reflected edge rays more.

In the embodiment shown, the photo-detectors 23 are consecutively mounted in a row in the depth direction (Arrow A) whereby they are able to receive all the light rays 22. The detectors 23 are juxtaposed in a support 27. Together with electronic components, the photo-detectors 23 are molded into the support 27, simultaneously fitted with contacts 28 electrically connected to the detectors 23 and electrically connected by leads 35 to the amplifier 24. Electric leads 34 run from the amplifier 24 to the control unit 26. The support 27 illustratively is bonded to the housing 19.

The filling detector 8 cooperates with an analyzer 29 to process a plot of the signals received from the photo-detectors 23 to allow determining a filling position, that is the position of a filling in the depth direction (direction A) of the guide duct in the vicinity of the filling detector 8. Illustratively the analyzer 29 will be part of the control unit 26. The electric leads 34 run to the analyzer 29. A display 55 is connected to the analyzer 29 and shows a plot of the position of the filling(s) and thereby allows an operator to monitor the filling position(s) when setting up the equipment.

Figure 5:
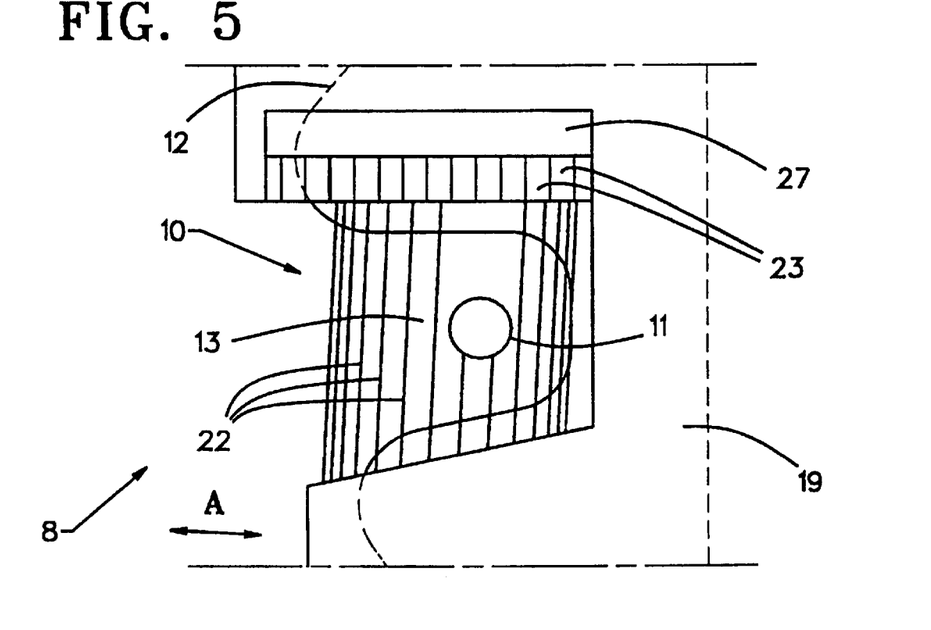
FIG. 5 is a cutaway of a guide duct fitted with a filling detector and containing a filling.
Figure 6:
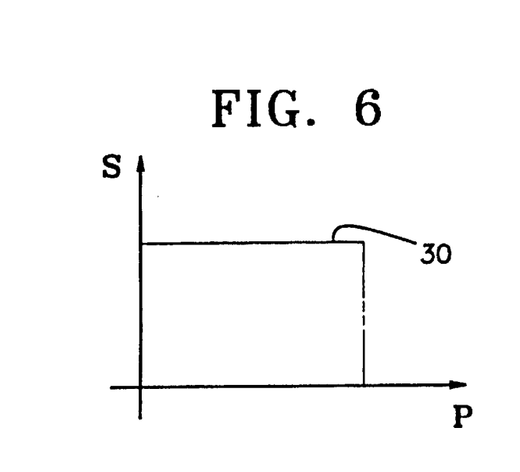
FIG. 6 is a plot of signals received by a filling detector in the absence of a filling.

The processing of the signals from the photo-detectors 23 for the purpose of plotting the position of a filling in the guide duct 10 in the vicinity of the filling detector 8 is shown in FIGS. 5 through 9. The plots show the (amplified) signal S against the guide-duct depth P. The plot 30 of FIG. 6 is for the absence of a filling and corresponds almost to a straight line because all light rays—which are of approximately identical light intensities—were received. Even though the received signals are shown as a continuous line, actually they are a row of adjacent short line segments of which each length corresponds to the width of the particular detectors 23. If for instance twenty photo-detectors 23 are mounted adjacent to each other, they will then produce twenty corresponding short signal segments which together form a nearly continuous line. The width of the photo-detectors 23 in the depth direction of the guide duct 10 (direction A) is comparatively minor. It is less than the diameter of a typical filling being processed.

Figure 7:
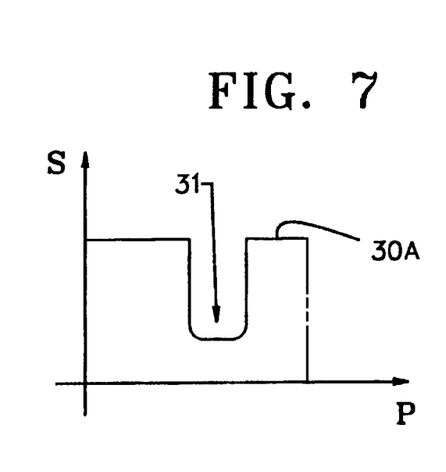
FIG. 7 is a plot of the signals received by a filling detector in the presence of one filling.
Figure 8:
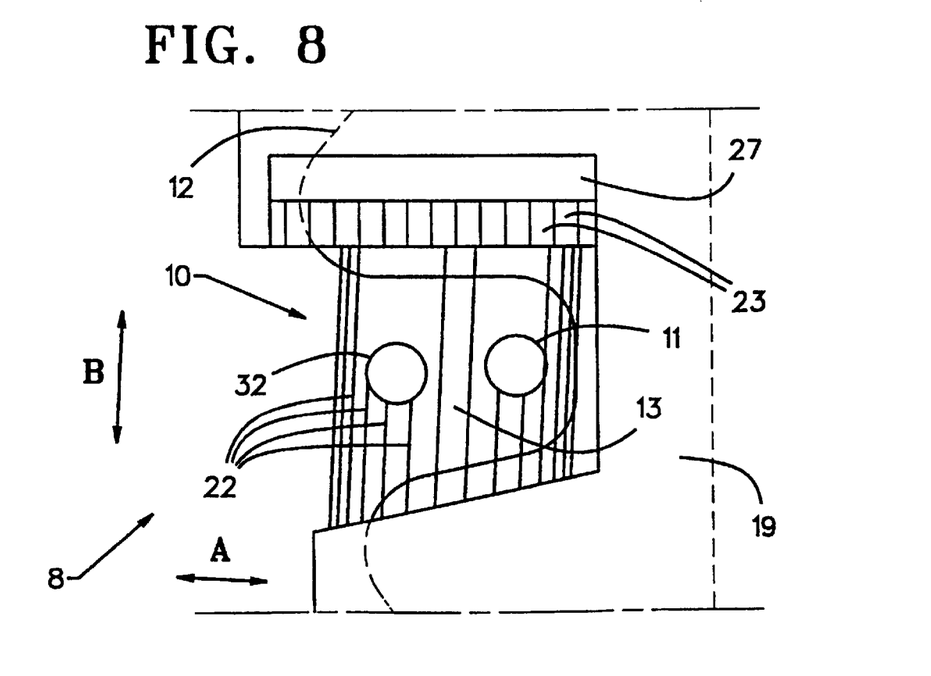
FIG. 8 is a cutaway of a guide duct holding two fillings and fitted with a filling detector.
Figure 9:
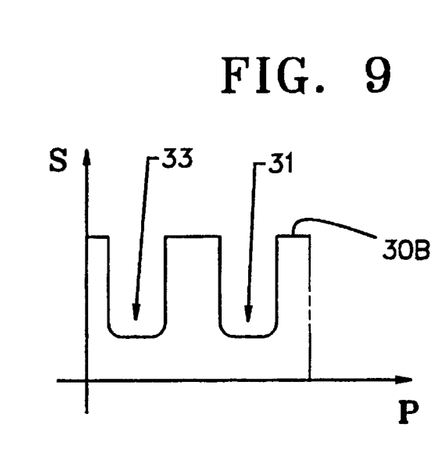
FIG. 9 is a plot of the signals received by a filling detector from two fillings.

If a filling 11 or 32 is present in the vicinity of the filling detector 8, some of the light rays 22 will be interrupted and the photo-detectors masked by the filling 11, 32 shall receive significantly less light. FIG. 7 shows a corresponding plot 30A. In the zone of those detectors 23 to which the light rays 22 were interrupted by the filling 11 or 32, said interrupted rays no longer directly reach the photo-detectors 23 and the emitted signal is in substantially attenuated form. This plot 30A can be analyzed by ascertaining the particular segment 31 of a signal which is substantially attenuated relative to the other zones. Each signal emitted by this detector 23 is then compared with that emitted from it in the absence of a filling. If the signal is less than for absence of signal, a filling will be present. By analyzing which detector 23 emits a lesser signal, the particular position of the filling 11, 32 which it assumes relative to the depth of the guide duct 10 can be determined. If no weaker signal is received, no filling 11, 12 is in the vicinity of the filling detector 8.

The position of a filling 11 or 32 can be determined several times consecutively in the vicinity of, and by, the detector 8 and using the analyzer 29. Thereby it is feasible to ascertain the changes in time of the position of the filling 11, 32 during a filling insertion. By using statistics, for instance implemented by the analyzer 29, a mean position of the filling 11 or 32 can be determined as well as the displacement by which a filling 11 or 32 changes its position relative to said mean position. Illustratively in this case it is possible to empirically adjust the control of compressed air to the main jet nozzles 4, 5 and to the auxiliary jet nozzles 6, and/or the configuration of the auxiliary jet nozzles 6 in such manner that the range of displacement shall be minimized. Each parameter may be varied and the effect of such a change on displacement then may be ascertained to globally optimize filling insertion.

The filling detector 8 of the invention is also suited for looms inserting two or more fillings simultaneously into a shed. For instance two fillings 11, 32 each are moved by associated main jet nozzles 4, 5 into the guide duct 10 and then are blown farther by the auxiliary jet nozzles 6 through this guide duct 10. As illustratively shown in FIG. 8, two fillings 11, 32 in that case will be in the vicinity of the filling detector 8 in the guide duct 10. This scenario leads to a plot 30B of FIG. 9 comprising two segments 31, 33 wherein the received signals are substantially attenuated relative to the other portions. The received-signal plot 30B can be analyzed in such manner as to determine whether two mutually distinct segments 31, 33 are present that indicate the presence of two fillings 11, 32.

Because sometimes the two fillings 11, 32 in the vicinity of the filling detector 8 may be superposed in a direction B perpendicular to the direction A, the filling detector 8 of the invention might then only detect the presence of one filling. However, because the fillings 11, 32 move erratically, namely both in the direction A as well as in the direction B, there shall always be a time at which the fillings 11, 32 are mutually adjacent and thereby result in two mutually distinct segments 31, 33 in the plot. Consequently the filling positions are checked several times consecutively to unambiguously determine whether two fillings 11, 32 are present in the guide duct, namely when at one or at several times two segments 31, 33 different from each other are determined by the plot 30B.

The same mode may be used also when three or more fillings are inserted at the same time. In the case of three fillings, three different segments will be looked for in the plot. In the case of four fillings, four different segments will be looked for in the plot, etc. Moreover the positional changes in time of several fillings can be ascertained simultaneously, for instance their dispersions about a mean value.

Because the light rays 22 essentially are collimated, the invention offers the advantage that the signals received by the photo-detectors 23 will be sharply different when the fillings 11, 32 break the light rays. Moreover the substantially collimated light rays 22 also offer the advantage that the height positions of the fillings 11, 32 in the guide duct 10 (direction B in FIG. 2) only little affect the signals received from the photo-detectors 23 only a little.

Figure 10:
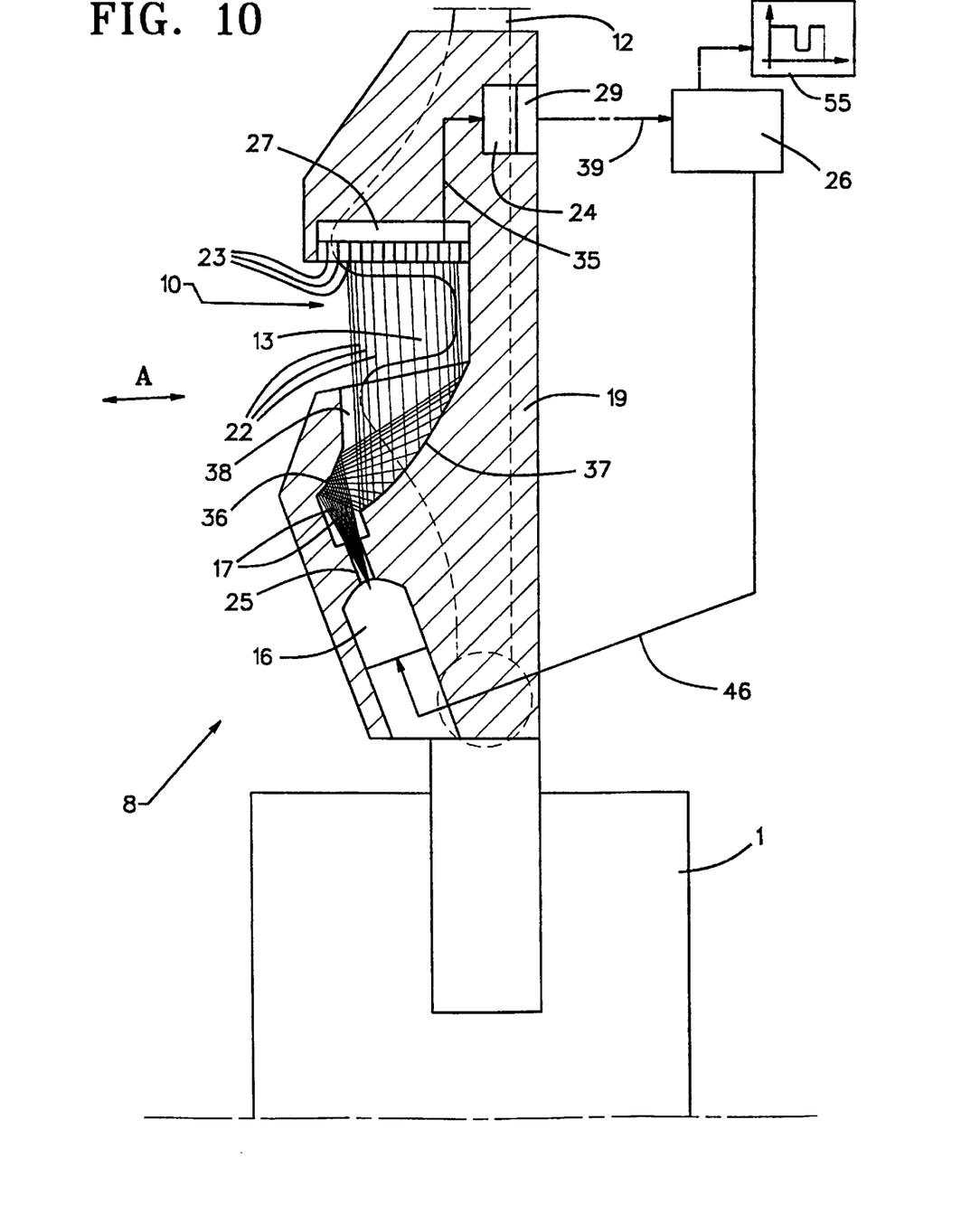
FIG. 10 is a section similar to that of FIG. 2 of a modified design of a filling detector.

In the embodiment of FIG. 10, the photo-detectors 23 of the filling detector 8 are mounted above the guide duct 10 in the manner of the embodiment of FIGS. 2 through 4. The light rays 17 of the light source 16 however are deflected by mirrors 36 and 37 and are guided from below to above through the guide duct 10. The mirrors 36 and 37 are mounted in a recess 38 of the housing 19. The analyzer 29 is mounted in the vicinity of the amplifier 24 in the housing 19 and is connected by electric leads 39 to the control unit 26. The filling detector 8 operates as in the embodiment of FIGS. 2 through 4.

Figure 11:
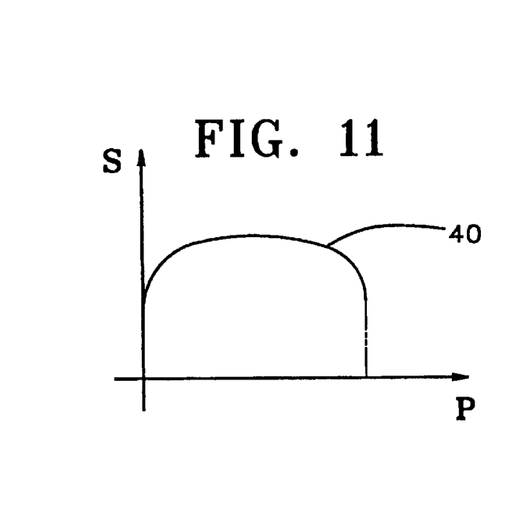
FIGS. 11–13 are plots of the signals received by the filling detector of FIG. 10 in the absence of a filling, in the presence of one filling and in the presence of two fillings.
Figure 12:
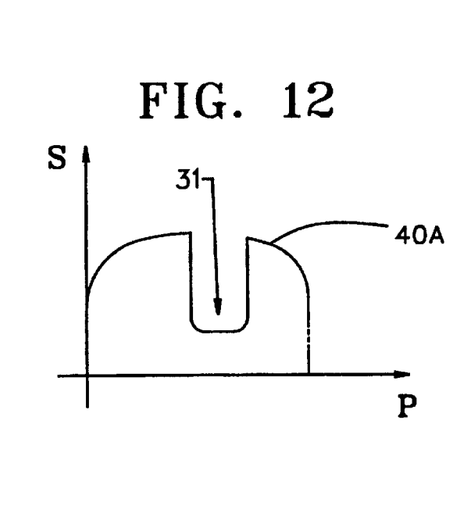
Figure 13:
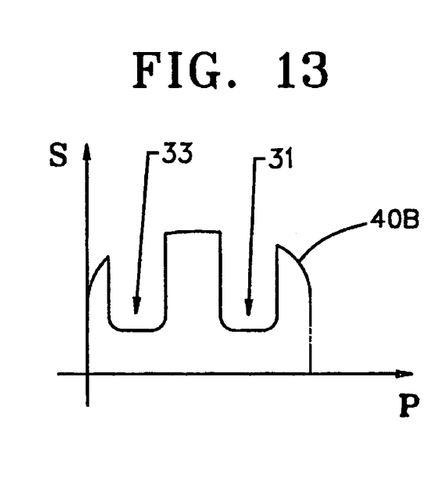

In the embodiment of FIG. 10, the set of light rays 22 varies in intensity over the depth of the guide duct 10 and accordingly, in the absence of a filling in the guide duct 10, the plot 40 of FIG. 11 will be seen. If a filling 11 or 32 of FIG. 5 is present, it results in a plot 40A shown in FIG. 12. The position of the filling 11 or 32 can be determined by comparing the plot 40A of FIG. 12 with the plot 40 of FIG. 11. If two fillings 11, 32 are present, there will be a plot 40B as in FIG. 13. In this case the position of the fillings 11, 32 can be determined by comparing the plot 40B of FIG. 13 with the plot 40 of FIG. 11. This filling detector 8 also allows determining the positions of the fillings 11, 32 at different times and in sequence and consequently the dispersion relative to a mean position or presence of two fillings 11, 32 may be ascertained.

In another variation (not shown) of the invention, the photo-detectors 23 are mounted underneath the guide duct 10 whereas the light rays 22 from the light source are guided in such a way that they pass from above through the guide duct 10 to the photo-detectors 23 below.

Furthermore the signals from the photo-detectors 23 can be guided directly, that is without passing through an amplifier 24, to the analyzer 29.

Figure 14:
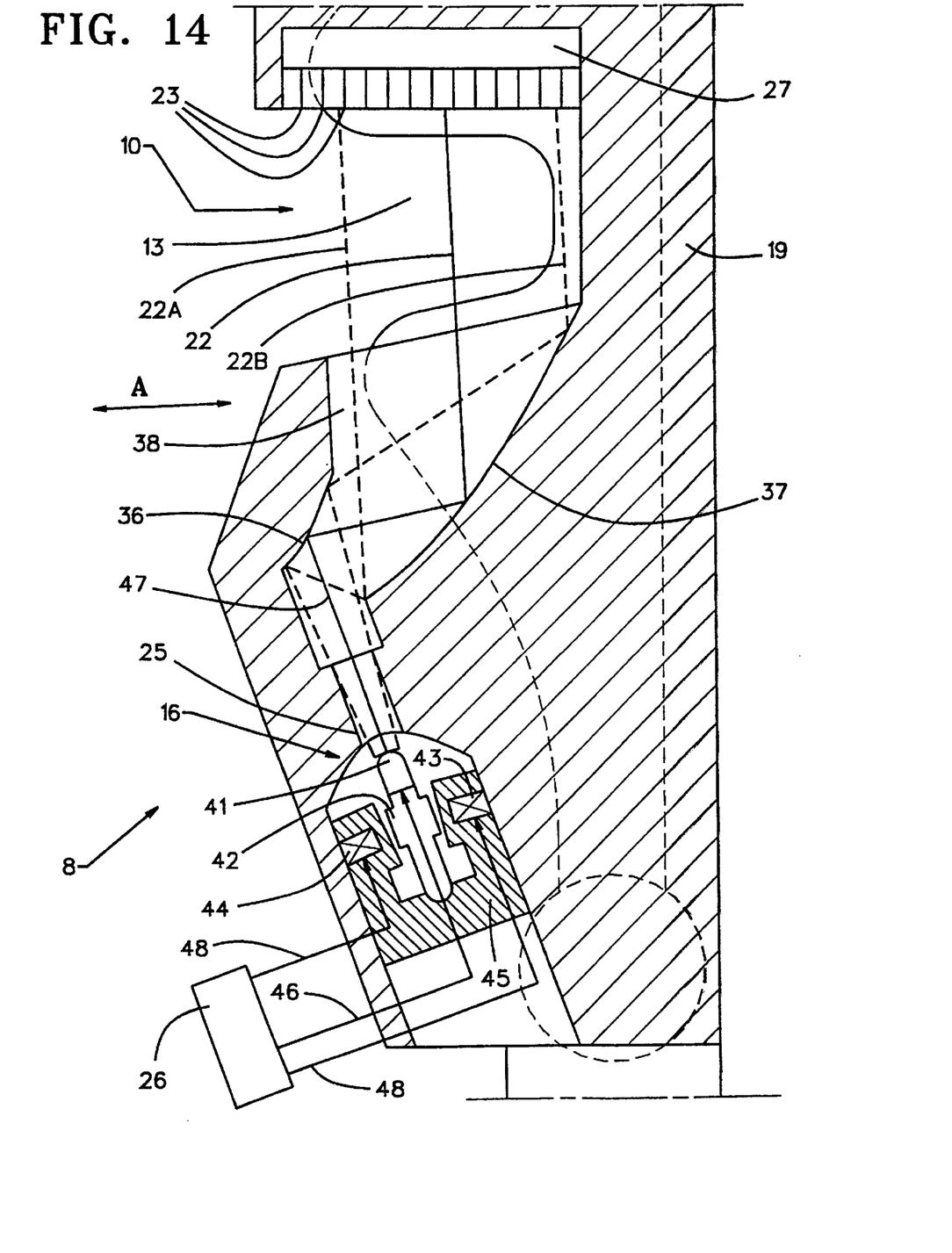
FIG. 14 is a section similar to that of FIG. 2 of another embodiment of a filling detector of the invention.

FIG. 14 shows an embodiment of a filling detector 8, the light source for which is a bulb 41 emitting a concentrated, focused light ray 47. The bulb 41 is fitted with a support 42 to allow moving it, and thus the focused light ray 47, to-and-fro in order to generate a reciprocating light ray. The support 42 cooperates with two electromagnets 43, 44 controlled from the control unit 26 through electric leads 48. The support 42 rests pivotably in a housing 45 also receiving the electromagnets 43, 44. Using the electromagnets 43, 44 to tilt the support 42, the light beam 47 of the bulb 41 moves to-and-fro. This light beam is so deflected by mirrors 36, 37 that it runs in the form of light rays 22 through the guide duct 10 in the direction of its depth, these light rays 22 being substantially collimated across the depth of the guide duct 10; that is, a light ray 22 is generated for each position of the support 42 and of the bulb 41 which runs through the guide duct 10 and which shall be substantially parallel to each other light ray 22 passing through the guide duct 10 for another position of the support 42 and the bulb 41. In this process the light rays 22 move between the zone defined by the outer light rays 22A and 22B. By operating a comparatively high frequency of tilting, an effect is achieved whereby a substantially continuous field of essentially parallel light rays 22 can be detected by the photo-detectors 23.

By appropriately designing the mirrors 36, 37, the rate of tilting the support 42 can be controlled in such manner that the light rays 22 shall sweep the guide duct 10 over its depth with nearly constant light intensity. Illustratively the tilting rate of the support 42 can be raised when the light ray 47 of the bulb 41 is directed at sites on the mirrors 36, 37 that focus the light rays more than when the light ray of the bulb 41 is aimed on other sites of the mirrors 36, 37. In the shown embodiment, therefore, the tilting rate of the support 42 will be relatively higher when this support is closer to the electromagnets 43, 44 than when it is mid-way between the electromagnets 43, 44 because the mirrors 36, 37 focus the light rays more near the edge of the guide duct 10 than at its center. This feature further prevents the light ray 47 being deflected toward the mirrors 36, 37 when the support 42 is very close to the electromagnets 43, 44 because at that time the speed of the support 42 approaches zero.

The depth of the guide duct 10 (direction A) denotes the direction transverse to the guide duct 10 and perpendicular to the drop wires 12 of the reed 2 and being essentially perpendicular to the light rays 22. The width or depth position of fillings 11, 32 is determined thereby, that is the position of the fillings 11, 32 in the transverse direction of the guide duct 10.

In an omitted embodiment of the invention, the position of the filling(s) is determined by two filling detectors of which the substantially collimated light rays cross each other. The position of the filling(s) is then determined in two directions, and as a result the absolute position of the filling(s) in the guide duct 10 can be determined geometrically.

Furthermore, besides their position, the thickness of the fillings 11, 32 can be determined from the plots 30A, 30B, 40A, 40B, by ascertaining the width of the segments 31, 33. As a result the filling detector 8 also allows ascertaining differences in thicknesses of the fillings 11, 32.

The invention is not restricted to blowing the fillings 11, 32 using compressed air from main jet nozzles 4, 5 and auxiliary jet nozzles 6 through the guide duct 10. The invention also applies when fillings are conveyed in different manners through the guide duct 10. Illustratively such conveyance may be implemented using water from a main nozzle configured in the manner of the main jet nozzles 4, 5 at the reed's insertion side 3, using a projectile or in another similar manner.

The dents 12, 14 also are not mandatorily of the shape shown in the drawings. Illustratively they may assume a shape as disclosed in U.S. Pat. No. 3,853,408.

In an embodiment (not shown) of the invention, a filling detector 8 is mounted between the auxiliary reed 9 and the stretching nozzle 15. Again, a filling detector 8 mounted in such manner may be used in addition to the filling detector 8 between the reed 2 and the auxiliary reed 9.

It is quite easy moreover to mount a filling detector 8 not on the batten 1 but in stationary manner on a loom frame not shown. In this case however the filling detector 8 must be configured in such manner that, in the approximately rearmost position of the batten 1, namely when the reed is far from the beat-up line and a filling 11, 32 is inserted in the guide duct 10, this guide duct 10 and the filling detector 8 shall be substantially flush.

Besides a prism 18 and/or mirrors 20, 21, the filling detector 8 also may contain in addition one or more lenses to produce light rays 22 which are essentially directed in collimated manner through the guide duct 10.

Obviously modifications of the above described method and/or of the illustrative embodiments of filling detector can be carried out within the skill of experts without thereby avoiding the scope of protection which is to be determined solely by the attached claims.

What is claimed is:

1. A method for optically monitoring at least one filling (11, 32) inserted into a guide duct (10) of a loom comprising:

providing a plurality of photo-detectors (23) positioned substantially transverse to a lengthwise direction of the guide duct (10);

inserting the at least one filling (11, 32) into the guide duct (10);

directing substantially collimated light rays (22) transverse to the lengthwise direction of the guide duct (10) onto the photo-detectors (23);

detecting with the photo-detectors (23) the interruption of the light rays (22) caused by the insertion of the at least one filling (11, 32) into the guide duct (10); and detecting a position of the at least one filling (11, 32) when the at least one filling (11, 32) is inserted into the guide duct (10).

2. The method as claimed in claim 1, wherein the step of inserting the at least one filling (11, 32) comprises inserting two or more of the fillings (11, 32) substantially simultaneously, and the step of detecting a position comprises detecting both the position and presence of each of the two or more of the fillings (11, 32).

3. The method as claimed in claim 1, wherein the step of detecting a position comprises consecutively detecting at least twice during the filling insertion the position of the at least one filling (11, 32).

4. The method as claimed in claim 2, wherein the step of inserting at least one filling into the guide duct (10) comprises inserting at least two fillings (11, 32) and the step of detecting interruption of light rays (22) comprises distinguishing signals generated by the photo-detectors for presence or absence of segments (31, 33), wherein the signals generated by the photo-detectors weaker than the signals generated by the photo-detectors in the absence of the segments (31, 33).

5. The method as claimed in claim 1, further comprising the step of displaying and/or recording the position, including changes in the position, of the at least one filling (11, 32) during each insertion of the at least one filling (11, 32).

6. A loom filling detector for use in conjunction with a guide duct (10) arranged to receive at least one filling (11, 32), comprising:

a plurality of photo-detectors (23);

a source for generating substantially collimated light rays (22) that travel transverse to the direction of the guide duct (10) onto the photo-detectors (23);

the photo-detectors (23) positioned laterally adjacent the guide duct and arranged to detect and generate signals responsive to the interruption of the light rays (22) caused by the at least one filling (11, 32) traveling through the light rays (22); and an analyzer (29) connected to the photo-detectors (23) and arranged to process the signals generated by the photo-detectors and thereby determine the position of the at least one filling (11, 32).

7. The filling detector as claimed in claim 6, wherein the analyzer (29) detects changes in the positions of the fillings (11, 32).

8. The filling detector as claimed in claim 6, wherein a display (55) that shows the positions of the fillings (11, 32) in the guide duct (10) is connected to the analyzer (29) and/or a recorder that records the filling positions is connected to the analyzer (29).

9. The filling detector as claimed in claim 6, wherein a lighting device (41) generates substantially collimated light rays (22) and includes deflecting elements (18, 20, 21; 36, 37) that spread the light rays (22) transversely to the guide duct (10) in such manner that light intensity is approximately constant across the guide duct.

10. The filling detector as claimed in claim 6, wherein a lighting device (41) generates a focused light ray, and a device (42, 43, 44) generates a reciprocating motion of the light ray (47) to transversely scan the guide duct (10).

11. The method as claimed in claim 2, wherein the step of detecting a position comprises consecutively detecting at least twice during the filling insertion the position of the at least one filling (11, 32).

* * * * *